(12) United States Patent
Simonetti et al.

(10) Patent No.: US 8,876,952 B2
(45) Date of Patent: Nov. 4, 2014

(54) METHOD OF REMOVING MERCURY FROM A FLUID STREAM USING HIGH CAPACITY COPPER ADSORBENTS

(75) Inventors: Dante A. Simonetti, Palatine, IL (US); Vladislav I. Kanazirev, Arlington Heights, IL (US); Thomas J. Traynor, Vernon Hills, IL (US)

(73) Assignee: UOP LLC, Des Plaines, IL (US)

( * ) Notice: Subject to any disclaimer, the term of this patent is extended or adjusted under 35 U.S.C. 154(b) by 94 days.

(21) Appl. No.: 13/367,219

(22) Filed: Feb. 6, 2012

(65) Prior Publication Data
US 2013/0202503 A1 Aug. 8, 2013

(51) Int. Cl.
*B01D 53/02* (2006.01)
(52) U.S. Cl.
USPC ............................................. 95/134; 96/108
(58) Field of Classification Search
USPC ............................................. 95/134; 96/108
See application file for complete search history.

(56) References Cited

U.S. PATENT DOCUMENTS

| | | | | |
|---|---|---|---|---|
| 4,094,777 A * | 6/1978 | Sugier et al. | ................. | 210/670 |
| 4,902,662 A * | 2/1990 | Toulhoat et al. | .............. | 502/216 |
| 4,911,825 A | 3/1990 | Roussel et al. | | |
| 5,110,480 A | 5/1992 | Yan | | |
| 5,120,515 A | 6/1992 | Audeh et al. | | |
| 5,190,908 A | 3/1993 | Audeh et al. | | |
| 5,354,357 A * | 10/1994 | Markovs et al. | ................ | 75/670 |
| 7,645,306 B2 | 1/2010 | Kanazirev | | |
| 2008/0184884 A1* | 8/2008 | Jadhav | ........................... | 95/134 |
| 2009/0155148 A1 | 6/2009 | Kanazirev | | |

FOREIGN PATENT DOCUMENTS

| | | |
|---|---|---|
| EP | 0480603 A2 | 4/1992 |
| GB | 2428598 A | 2/2007 |
| SU | 393212 A | 12/1973 |
| WO | 2008020250 A1 | 2/2008 |
| WO | 2010061212 A1 | 6/2010 |
| WO | 2011021024 A1 | 2/2011 |
| WO | 2011081836 A2 | 7/2011 |

\* cited by examiner

*Primary Examiner* — Christopher P Jones
(74) *Attorney, Agent, or Firm* — Mark Goldberg

(57) ABSTRACT

A method of removing mercury from a fluid stream comprising contacting the fluid stream with a sorbent comprising cupric sulfide. The cupric sulfide is formed from direct sulfidation of copper carbonate, without thermal decomposition of the copper carbonate to an oxide, at a temperature less than about 150° C.

19 Claims, 2 Drawing Sheets

METHOD OF REMOVING MERCURY FROM A FLUID STREAM USING HIGH CAPACITY COPPER ADSORBENTS

FIELD OF THE INVENTION

The disclosure relates in general to the removal of contaminants from hydrocarbon liquids and gases. In certain embodiments, the disclosure relates to the use of a copper-based sorbent to remove mercury from hydrocarbon streams. In certain embodiments, the disclosure relates to the use of a high capacity sorbent comprising a copper sulfide compound, where the copper sulfide compound was produced by way of direct sulfidation of a copper oxysalt.

BACKGROUND OF THE INVENTION

Hydrocarbon fluid streams, including both liquid and gas streams, are often contaminated with mercury compounds. Sorbents containing supported metal sulfides, such as copper sulfide (CuS), have been used to scavenge mercury from hydrocarbon fluid streams by reaction 1.

$$2CuS + Hg \rightarrow HgS + Cu_2S \tag{1}$$

For example, U.S. Pat. No. 4,094,777 describes a solid mass that contains a carrier and sulfided copper as an absorbent for mercury from a gas or a liquid. CuS based materials for Hg removal are offered by Axens, Johnson Matthey and others for applications in the natural gas and hydrocarbon industries.

Prior art methods of producing copper sulfide sorbents include a two-step process. A copper carbonate is first decomposed to cupric oxide and the cupric oxide is subsequently sulfided to produce the active copper sulfide component of the sorbent. The decomposition of copper carbonate and the sulfidation of copper oxide requires relatively high temperatures, resulting in the agglomeration or clumping of the active component of the sorbent. The reduction of surface area limits the utilization of the active component. High utilization of the active copper sulfide component is desirable to decrease adsorbent bed volume and/or increase the adsorbent service lifetime. Accordingly, there is a need for higher capacity mercury sorbents that (i) are capable of scavenging more mercury per quantity of active component and/or (ii) have higher levels of active component utilization than prior art compositions and methods.

SUMMARY OF THE INVENTION

A method of removing mercury from a fluid stream is presented. The method comprises contacting the fluid stream with a sorbent comprising cupric sulfide. The cupric sulfide is formed from direct sulfidation of copper carbonate, without thermal decomposition of the copper carbonate to an oxide, at a temperature of less than about 150° C.

DETAILED DESCRIPTION OF PREFERRED EMBODIMENTS

Figure 1:
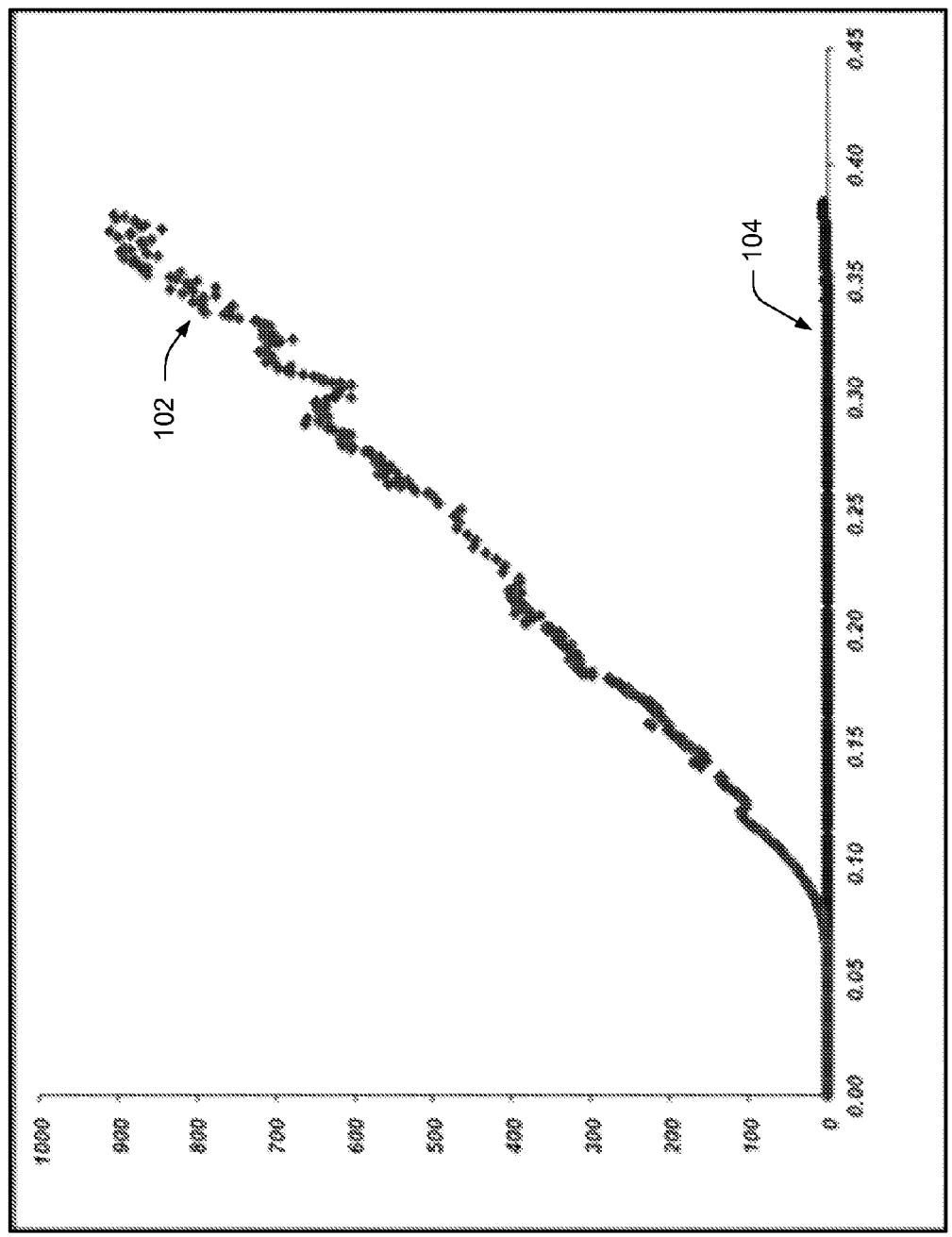
FIG. 1 is a graph of breakthrough curves for a prior art adsorbent and one embodiment of Applicants' sorbent, each having a 7×14 mesh size.

The invention is described in preferred embodiments in the following description with reference to the Figures, in which like numerals represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The terms sorbent, adsorbent, and absorbent as used herein refer to the ability of a material to take in or soak up liquid or gas components on the surface thereof or to assimilate such components into the body thereof.

Methods of producing copper-based sorbents, and sorbents produced by such methods, are presented. In one embodiment, Applicants' sorbent comprises a copper material disposed within a support material. In various embodiments, the sorbent comprises a copper sulfide disposed within a support material. In various embodiments, the copper sulfide is cupric sulfide (CuS). In various embodiments, the copper sulfide is cuprous sulfide ($Cu_2S$).

In various embodiments, the support material is a metal oxide selected from the group consisting of alumina, silica, silica-aluminas, silicates, aluminates, silico-aluminates such as zeolites, titania, zirconia, hematite, ceria, magnesium oxide, and tungsten oxide. In one embodiment, the support material is alumina. In some embodiments, the support material is carbon or activated carbon. In certain embodiments, Applicants' sorbent does not comprise a binder.

In various embodiments, the alumina support material is present in the form of transition alumina, which comprises a mixture of poorly crystalline alumina phases such as "rho," "chi" and "pseudo gamma" aluminas which are capable of quick rehydration and can retain substantial amounts of water in a reactive form. An aluminum hydroxide $Al(OH)_3$, such as gibbsite, is a source for preparation of transition alumina. The prior art industrial process for production of transition alumina includes milling gibbsite to 1-20 microns particle size followed by flash calcination for a short contact time as described in the patent literature such as in U.S. Pat. No. 2,915,365. Amorphous aluminum hydroxide and other naturally found mineral crystalline hydroxides e.g., Bayerite and Nordstrandite or monoxide hydroxides, AlOOH, such as Boehmite and Diaspore can be also used as a source of transition alumina. In certain embodiments, the BET surface area of this transition alumina material is about 300 $m^2/g$ and the average pore diameter is about 45 angstroms as determined by nitrogen adsorption, resulting in a porous sorbent.

In various embodiments, a solid oxysalt of a transition metal is used as a starting component of the sorbent. "Oxysalt," by definition, refers to any salt of an oxyacid. Sometimes this definition is broadened to "a salt containing oxygen as well as a given anion." FeOCl, for example, is regarded as an oxysalt according this definition.

In certain embodiments, the oxysalt comprises one or more copper carbonates. In certain embodiments, the oxysalt comprises one or more basic copper carbonates. Basic copper carbonates, such as $Cu_2(OH)_2CO_3$, can be produced by precipitation of copper salts, such as $Cu(NO_3)_2$, $CuSO_4$ and $CuCl_2$, with sodium carbonate. In one embodiment, a synthetic form of malachite, a basic copper carbonate, produced by Phibro Tech, Ridgefield Park, N.J., is used as a component of the sorbent.

Depending on the conditions used, and especially on washing the resulting precipitate, the final material may contain some residual product from the precipitation process. In the case of the $CuCl_2$ raw material, sodium chloride is a side product of the precipitation process. It has been determined that a commercially available basic copper carbonate that had both residual chloride and sodium exhibited lower stability towards heating and improved resistance towards reduction than other commercial basic copper carbonates that were practically chloride-free.

In one embodiment, the particle size of the green sorbent beads (i.e., the basic copper carbonate particles) is approximately in the range of that of the transition alumina, namely 1-20 microns. In other embodiments, the green sorbent bead comprises the oxysalt Azurite, $Cu_3(OH)_2(CO_3)_2$. In other embodiments, the green sorbent bead comprises an oxysalt of copper, nickel, iron, manganese, cobalt, zinc or a mixture thereof.

In certain embodiments, the green sorbent bead comprises between about 5 mass percent to about 85 mass percent copper, calculated as CuO on a volatile-free basis. In one embodiment, the green sorbent bead comprises about 70 mass percent copper.

The sorbent is produced by exposing the green sorbent bead to a sulfiding environment. In various embodiment, the sulfiding environment comprises hydrogen sulfide ($H_2S$), other organic or inorganic substances capable of releasing $H_2S$ under thermal treatment, such as without limitation dimethyl disulfide or polysulfides, or a combination thereof. In one embodiment, the green sorbent bead is sulfided at temperatures less than about 150° C. In one embodiment, the green sorbent bead is sulfided at temperatures between about 100° C. and about 150° C. The copper carbonate is directly sulfided without formation of a copper oxide intermediate. In certain embodiments, after the sulfiding step, the resulting sorbent comprises no residual copper carbonate. In certain embodiments, after the sulfiding step, the resulting sorbent comprises no copper oxide.

In certain embodiments, the sorbent comprises about 10 mass percent to about 80 mass percent copper sulfide. In certain embodiments, the sorbent comprises about 5 mass percent to about 23 mass percent sulfur in the form of copper sulfide. In certain embodiments, the sorbent comprises about 12 mass percent to about 18 mass percent sulfur in the form of copper sulfide. In certain embodiments, the sorbent comprises about 14 mass percent sulfur in the form of copper sulfide.

In certain embodiments, the final sorbent beads have a diameter (for spherical beads) or maximum width (for irregular shaped beads) of about 1 mm to about 10 mm. In certain embodiments, the final sorbent beads have a diameter or maximum width of about 1.2 mm to about 5 mm.

In various embodiments, the final sorbent beads are porous (i.e., have a plurality of pores and voids extending therethrough). In certain embodiments, the pore volume of the final sorbent beads is at least 0.12 $cm^3/g$. In various embodiments, the final sorbent beads have a bulk density of between about 640 $kg/m^3$ (40 $lbs/ft^3$) to about 1280 $kg/m^3$ (80 $lbs/ft^3$). In various embodiments, the final sorbent beads have a bulk density of 880 $kg/m^3$ (55 $lbs/ft^3$) to about 1150 $kg/m^3$ (72 $lbs/ft^3$).

In various embodiments, the final sorbent beads are disposed within a flow reactor configuration and exposed to a hydrocarbon fluid (i.e., gas or liquid) stream. In various embodiments, the fluid stream comprises between about 0.1 parts per billion (ppb) to about 1000 ppb mercury.

The crystal size of the copper sulfide formed by one embodiment of Applicants' method as compared to crystals produced by prior art methods is set forth in Table 1 below. The crystal size is determined using X-ray powder diffraction (XRD) and the Scherrer equation (1), where λ is the shape factor, is the x-ray wavelength, β is the line broadening at half the maximum peak intensity (FWHM) in radians, θ is the Bragg angle, and τ is the mean size of the crystalline domains, which may be smaller or equal to the grain size.

$$\tau = \frac{K\lambda}{\beta \cos\theta} \quad (1)$$

TABLE 1

| Adsorbent Type | Dimension at 27.2°2θ (1, 0, 0) in Å | Dimension at 32.9°2θ (0, 0, 6) in Å |
| --- | --- | --- |
| Prior Art CuS Adsorbent | 287 | 166 |
| New CuS Adsorbent Produced by Applicants' Method | 278 | 79 |

The first row of Table 1 represents 7×14 mesh beads of a prior art adsorbent produced by a two-step process where copper carbonate is first decomposed to a copper oxide and the copper oxide sulfided to a copper sulfide. The prior art absorbent has 37 mass percent CuS.

The second row of Table 1 represents 7×14 mesh beads produced by one embodiment of Applicants' method of direct sulfidation of a basic copper carbonate and having 75 mass percent CuS. The crystallite dimensions across vector (0,0,6) in Table 1 for adsorbents produced by Applicants' method are less than 50% of the corresponding dimensions for the prior art sample. The dimensions are presented in angstroms. Smaller crystallite dimensions result in greater surface area available for mercury scavenging and, therefore, higher adsorbent performance. In one embodiment, the crystallite size of the cupric sulfide measured on a (0,0,6) plane is less than 100 angstroms. In one embodiment, the crystallite size of the cupric sulfide measured on a (0,0,6) plane is less than 80 angstroms.

Referring to FIG. 1, a graph comparing the breakthrough curve of a prior art adsorbent against one embodiment of Applicants' adsorbent is presented. The x-axis represents the loading of the adsorbent in a test chamber in grams of mercury to grams of sulfur (g Hg/g S). The y-axis represents the concentration of mercury at the outlet of the test chamber in micrograms of mercury per cubic meter ($\mu g/m^3$).

Curve 102 represents a prior art adsorbent with a 7×14 mesh size (beads having a minimum dimension of smaller than 1.2 mm and greater than 2.8 mm). Below a loading of about 0.07 g Hg/g S, the prior art sorbent adsorbed all mercury, as indicated by the absence of mercury at the test chamber outlet. Above a loading of about 0.07 g Hg/g S, the prior art sorbent was unable to adsorb the mercury flowing through the test chamber, as indicated by the presence of mercury at the outlet. The amount of mercury measured at the outlet continued to increase as the mercury loading of the adsorbent beads increased.

Curve 104 represents Applicants' high-capacity sorbent beads with a 7×14 mesh size. Applicants' high-capacity sorbent beads were able to fully absorb mercury within the test chamber, up to a loading greater than about 0.35 g Hg/g S, where a very small amount of mercury was detected at the outlet.

Figure 2:
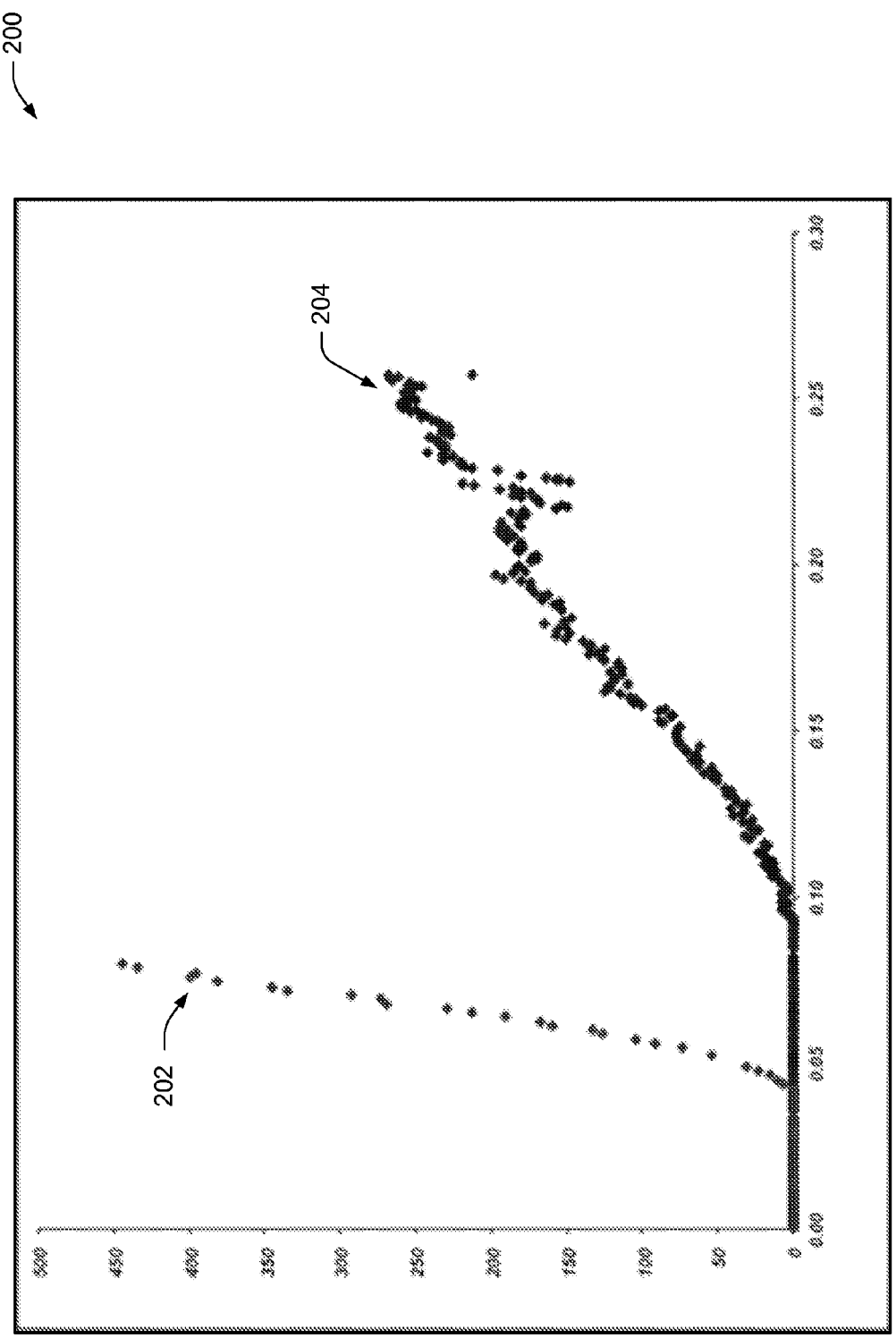
FIG. 2 is a graph of breakthrough curves for a prior art absorbent and one embodiment of Applicants' sorbent, each having a 5×8 mesh size.

Referring to FIG. 2, a graph comparing the breakthrough curve of a prior art adsorbent against another embodiment of Applicants' adsorbent is presented. The x-axis represents the loading of the adsorbent in a test chamber in grams of mercury to grams of sulfur (g Hg/g S). The y-axis represents the concentration of mercury at the outlet of the test chamber in micrograms of mercury per cubic meter ($\mu g/m^3$).

Curve 202 represents a prior art adsorbent with a 5×8 mesh size (beads having a minimum dimension of smaller than 4.0 mm and greater than 2.4 mm). Below a loading of about 0.04 g Hg/g S, the prior art sorbent adsorbed all mercury, as indicated by the absence of mercury at the outlet. Above a loading of about 0.04 g Hg/g S, the prior art sorbent was unable to adsorb the mercury flowing through the test chamber, as indicated by the presence of mercury at the outlet. Curve 202 increases about linearly at a first slope above a loading of about 0.04 g Hg/g S.

Curve 204 represents Applicants' high-capacity sorbent beads with a 5×8 mesh size. Applicants' high-capacity sorbent beads were able to fully absorb mercury within the test chamber, up to a loading of about 0.09 g Hg/g S. Above a loading of about 0.09 g Hg/g S, curve 204 increases about linearly at a second slope, where the first slope is at least two times the second slope.

The following Example is presented to further illustrate to persons skilled in the art how to make and use the invention. This Example is not intended as a limitation, however, upon the scope of Applicant's invention.

EXAMPLE

A mixture of a copper oxysalt and a support material is provided. In one embodiment, the copper oxysalt is basic copper carbonate, $Cu_2(OH)_2CO_3$ and the support material is alumina powder capable of rehydration. In different embodiments, the copper content of the mixture, calculated as CuO on a volatile-free basis, is between about 5 mass percent and about 85 mass percent. In one embodiment, the copper content of the mixture is about 70 mass percent.

Green sorbent beads are formed from the mixture. As used herein, "green sorbent beads" refer to beads containing the copper oxysalt before any sulfidation and "activated sorbent beads" refer to beads where at least a portion of the copper oxysalt has been sulfided. In one embodiment, the beads are formed by nodulizing the mixture in a rotating pan nodulizer while spraying with a liquid. In one embodiment, the liquid comprises water. In one embodiment, the liquid comprises a solution of water and a halide salt. In one embodiment, the halide salt is sodium chloride. In one embodiment, the solution comprises an about 1 mass percent to about 3 mass percent solution of sodium chloride.

In another embodiment, the green sorbent beads are formed by agglomeration. In another embodiment, the green sorbent beads are formed by extrusion. Those skilled in the art will appreciate that other methods may be performed to produce regular- or irregular-shaped beads, with or without a halide salt, that fall within the scope of Applicants' invention.

The green sorbent beads are cured and dried. In one embodiment, the curing occurs at about 60° C. In one embodiment, the beads are dried in a moving bed activator at temperatures at or below 175° C. In one embodiment, the activated sorbent beads comprise about 0.5 mass percent to about 0.8 mass percent chloride.

The green sorbent beads are activated by exposure to a sulfiding environment. As would be appreciated by those skilled in the art, the length of exposure, the composition of the sulfiding environment, and temperature are selected based on the desired composition of the active copper components in the final sorbet product. In certain embodiments, the sulfiding environment comprises hydrogen sulfide ($H_2S$). In various embodiments, the sulfiding environment comprises between about 0.0005 mole percent and 100 mole percent hydrogen sulfide ($H_2S$), the balance being an inert gas.

In one embodiment, the sulfidation occurs at between about 100° C. to about 150° C. In certain embodiments, the copper in the green material is fully sulfided. In one embodiment, the activated sorbent comprise about 37 mass percent CuS. In certain embodiments, the activated sorbent comprises between about 10 mass percent to about 80 mass percent CuS. The activated beads are then exposed to a hydrocarbon fluid stream containing sulfur- and/or mercury-containing materials.

The described features, structures, or characteristics of the invention may be combined in any suitable manner in one or more embodiments. In the above description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described, in detail to avoid obscuring aspects of the invention. In other words, the present invention may be embodied in other specific forms without departing from its spirit or essential characteristics. The described implementations are to be considered in all respects only as illustrative and not restrictive. The scope of the invention should, therefore, be determined not with reference to the above description, but instead should be determined with reference to the pending claims along with their full scope or equivalents, and all changes which come within the meaning and range of equivalency of the claims are to be embraced within their full scope.

What is claimed is:

1. A method of removing mercury from a fluid stream, comprising contacting said fluid stream with a sorbent comprising cupric sulfide, wherein said cupric sulfide is formed from direct sulfidation of copper carbonate, without thermal decomposition of the copper carbonate to an oxide, at a temperature less than about 150° C. and wherein a crystallite size of said cupric sulfide measured on a (0,0,6) plane is less than 100 angstroms.

2. The method of claim 1, wherein the sorbent comprises no residual copper carbonate.

3. The method of claim 2, wherein said sorbent comprises no copper oxide.

4. The method of claim 1, wherein said sorbent does not comprise a binder.

5. The method of claim 1, wherein said copper carbonate is $Cu_2(OH)_2CO_3$.

6. The method of claim 1, wherein said sorbent further comprises a metal oxide.

7. The method of claim 6, wherein said metal oxide is selected from the group consisting of alumina, silica, silica-aluminas, silicates, aluminates, silico-aluminates, zeolites, titania, zirconia, hematite, ceria, magnesium oxide, and tungsten oxide.

8. The method of claim 6, wherein said metal oxide comprises a transition alumina formed by the flash calcination of gibbsite.

9. The method of claim 7, wherein said sorbent comprises about 5 mass percent to about 23 mass percent sulfur in the form of cupric sulfide.

10. The method of claim 1, wherein said direct sulfidation comprises exposing said copper carbonate to a sulfiding environment.

11. The method of claim 10, wherein said sulfiding environment comprises hydrogen sulfide ($H_2S$).

12. The method of claim 11, wherein said sulfiding environment has a H$_2$S concentration of between about 0.0005 mole percent to about 100 mole percent.

13. The method of claim 1, wherein a crystallite size of said cupric sulfide measured on a (0,0,6) plane is less than 80 angstroms.

14. The method of claim 1, wherein said fluid stream comprises between about 0.1 ppb to about 1000 ppb elemental mercury.

15. The method of claim 1, wherein said sorbent is porous with a pore volume of at least 0.12 cm$^3$/g.

16. The method of claim 15, wherein said sorbent has a diameter (or maximum width) of between about 1 mm to about 10 mm.

17. The method of claim 16, wherein said sorbent has a diameter (or maximum width) of between about 1.2 mm to 5 mm.

18. The method of claim 1, wherein the bulk density of said sorbent is between about 640 kg/m$^3$ (40 lbs/ft$^3$) to about 1280 kg/m$^3$ (80 lbs/ft$^3$).

19. The method of claim 18, wherein the bulk density of said sorbent is between about 880 kg/m$^3$ (55 lbs/ft$^3$) to about 1150 kg/m$^3$ (72 lbs/ft$^3$).

* * * * *